(12) United States Patent
Bornzin et al.

(10) Patent No.: US 7,474,921 B1
(45) Date of Patent: Jan. 6, 2009

(54) ADJUSTABLE OVERDRIVE PACING

(75) Inventors: Gene A. Bornzin, Simi Valley, CA (US); Peter Boileau, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 562 days.

(21) Appl. No.: 10/868,732

(22) Filed: Jun. 14, 2004

(51) Int. Cl.
*A61N 1/362* (2006.01)

(52) U.S. Cl. ...................................... 607/14

(58) Field of Classification Search ............ 607/4, 607/14
See application file for complete search history.

(56) References Cited

U.S. PATENT DOCUMENTS

| | | | | |
|---|---|---|---|---|
| 4,712,555 | A | 12/1987 | Thornander et al. ... | 128/419 PG |
| 4,788,980 | A | 12/1988 | Mann et al. ........... | 128/419 PG |
| 4,940,052 | A | 7/1990 | Mann et al. ........... | 128/419 PG |
| 5,466,254 | A | 11/1995 | Helland ................. | 607/123 |
| 5,476,483 | A | 12/1995 | Bornzin et al. ........ | 607/17 |
| 6,058,328 | A | 5/2000 | Levine et al. ......... | 607/14 |
| 6,314,323 | B1 | 11/2001 | Ekwall .................. | 607/23 |
| 6,510,342 | B1 | 1/2003 | Park et al. | |
| 6,519,493 | B1 * | 2/2003 | Florio et al. .......... | 607/9 |
| 6,775,571 | B1 | 8/2004 | Kroll | |
| 6,907,287 | B1 * | 6/2005 | Bevan et al. .......... | 607/14 |
| 6,941,170 | B1 * | 9/2005 | Lu ....................... | 607/14 |
| 7,103,411 | B1 * | 9/2006 | Park et al. ............ | 607/14 |
| 7,127,292 | B2 * | 10/2006 | Warman et al. ....... | 607/25 |
| 7,164,944 | B1 * | 1/2007 | Kroll et al. ........... | 607/2 |
| 2005/0075701 | A1 * | 4/2005 | Shafer .................. | 607/72 |
| 2005/0245975 | A1 * | 11/2005 | Hettrick et al. ....... | 607/9 |

FOREIGN PATENT DOCUMENTS

| | | | |
|---|---|---|---|
| EP | 1110580 A2 | 6/2001 | |
| WO | WO 98/32489 | 7/1998 | |

OTHER PUBLICATIONS

NonFinal Office Action, mailed Nov. 8, 2005: Related U.S. Appl. No. 10/868,493.
NonFinal Office Action, mailed Aug. 31, 2006: Related U.S. Appl. No. 10/868,493.
Notice of Allowance, mailed Jul. 5, 2006: Related U.S. Appl. No. 10/868,493.
NonFinal Office Action, mailed Sep. 19, 2005: Related U.S. Appl. No. 10/868,331.
Final Office Action, mailed Jan. 11, 2006: Related U.S. Appl. No. 10/868,331.
NonFinal Office Action, mailed Mar. 31, 2006: Related U.S. Appl. No. 10/868,331.
Notice of Allowance, mailed Jun. 30, 2006: Related U.S. Appl. No. 10/868,331.
Advisory Action, mailed Feb. 27, 2006: Related U.S. Appl. No. 10/868,331.

\* cited by examiner

*Primary Examiner*—George R Evanisko
*Assistant Examiner*—Amanda Patton

(57) ABSTRACT

An exemplary method includes providing an overdrive pacing rate and, determining an incidence limit for incidence of intrinsic atrial activity events, as well as the incidence of intrinsic atrial activity events The exemplary, method further includes comparing the incidence of intrinsic atrial activity events to the incidence limit and, based at least on the comparing, deciding whether to adjust the overdrive pacing rate. According to this exemplary method, the incidence limit is optionally a function of overdrive pacing rate. Another exemplary method includes determining a dwell limit wherein the dwell limit is optionally a function of overdrive pacing rate. Other exemplary methods, devices, systems, etc., are also disclosed.

17 Claims, 11 Drawing Sheets

ADJUSTABLE OVERDRIVE PACING

CROSS-REFERENCE TO RELATED APPLICATIONS

This application is related to copending U.S. patent applications: 1) Ser. No. 10/868,493, titled "Adjustable Overdrive Pacing"; and 2) Ser. No. 10/868,331, titled "Adjustable Overdrive Pacing"; all applications filed concurrently herewith.

TECHNICAL FIELD

Subject matter presented herein generally relates to cardiac pacing and/or stimulation therapy. Various exemplary methods, devices, systems, etc., concern overdrive pacing and adjustments thereto.

BACKGROUND

Premature atrial contractions (PACs) occur when a site in the atria other than the sinus node develops automaticity of a rate greater than that of the sinus node. Such a site is called an ectopic focus. An ectopic focus can usurp control of the atria from the sinus node for one or a few consecutive beats causing a single PAC or a "salvo" of PACs. If the ectopic focus remains in control for a long period, this is referred to as a focal atrial tachycardia.

Some conventional pacemakers have an ability to respond to PACs. For example, some conventional pacemakers treat PACs that occur outside of the post-ventricular atrial refractory blanking period (PVARP) as sinus P-waves and respond by tracking PACs or, in non-tracking modes, by inhibiting output of atrial pacing stimuli. Further, if such a conventional pacemaker has enabled an atrial fibrillation (AF) suppression algorithm (e.g., dynamic atrial overdrive), PACs that occur outside of the PVARP typically trigger an increase in atrial overdrive pacing rate (e.g., in a manner similar to sinus P-waves that occur outside of the PVARP).

AF suppression algorithms generally request an increase atrial overdrive pacing rate only if a predetermined number of P-waves occur within a predetermined number of cycles. For example, a conventional AF suppression algorithm will request an increase in atrial overdrive pacing rate if two P-waves occur in 16 consecutive pacing cycles. In addition, the requested rate increase is typically based on a present pacing rate (e.g., 110% of the present rate).

After a programmable number of overdrive cycles at the increased rate, the AF suppression algorithm requests a gradual decrease or decay in overdrive rate, for example, until a request for another increase, or until the overdrive rate reaches the higher of a base rate and a sensor indicated rate. If request calls for a rate increase that increases the overdrive rate above a maximum allowed overdrive rate, then the overdrive rate is clipped to the maximum allowed overdrive rate.

Aforementioned algorithms, however, may respond inappropriately to repeated salvos of PACs. For example, repeated salvos of PACs can result in ever increasing rate requests that drive the overdrive rate up to the maximum allowed overdrive rate (e.g., typically equal to the maximum sensor rate in conventional pacemakers) and, once reached, request that the maximum rate is maintained for an extended period of time. Physiologic consequences of maintaining a high overdrive rate for an extended period of time are manifold and may include pain, annoyance, heightened catecholaminergic response (e.g., positive feedback) and even tachycardia-induced heart failure. Thus, while it may be appropriate for an algorithm to increase the overdrive pacing rate in response to PACs, because overdrive pacing may act to suppress PACs, conventional AF suppression algorithms typically do not produce the best outcome in patients that experience salvos of PACs. In essence, if PACs persist or are persistent, then extended overdrive pacing at a maximum rate may do little, if nothing, to improve cardiac function and, at worst, it may lead to a critical condition.

Overall, a need exists for algorithms that respond appropriately to PACs and/or other atrial events. Various exemplary methods, devices, systems, etc., are described below which may address aforementioned needs and/or other needs.

SUMMARY

An exemplary method includes providing an overdrive pacing rate, based at least in part on the overdrive pacing rate, determining an incidence limit for incidence of intrinsic atrial activity events, determining an incidence of intrinsic atrial activity events, comparing the incidence of intrinsic atrial activity events to the incidence limit and, based at least on the comparing, deciding whether to adjust the overdrive pacing rate. According to this exemplary method, the incidence limit is optionally a function of overdrive pacing rate. Another exemplary method includes determining a dwell limit wherein the dwell limit is optionally a function of overdrive pacing rate. Other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

The techniques described below are intended to be implemented in connection with any stimulation device that is configured or configurable to stimulate nerves and/or stimulate and/or shock a patient's heart.

Figure 1:
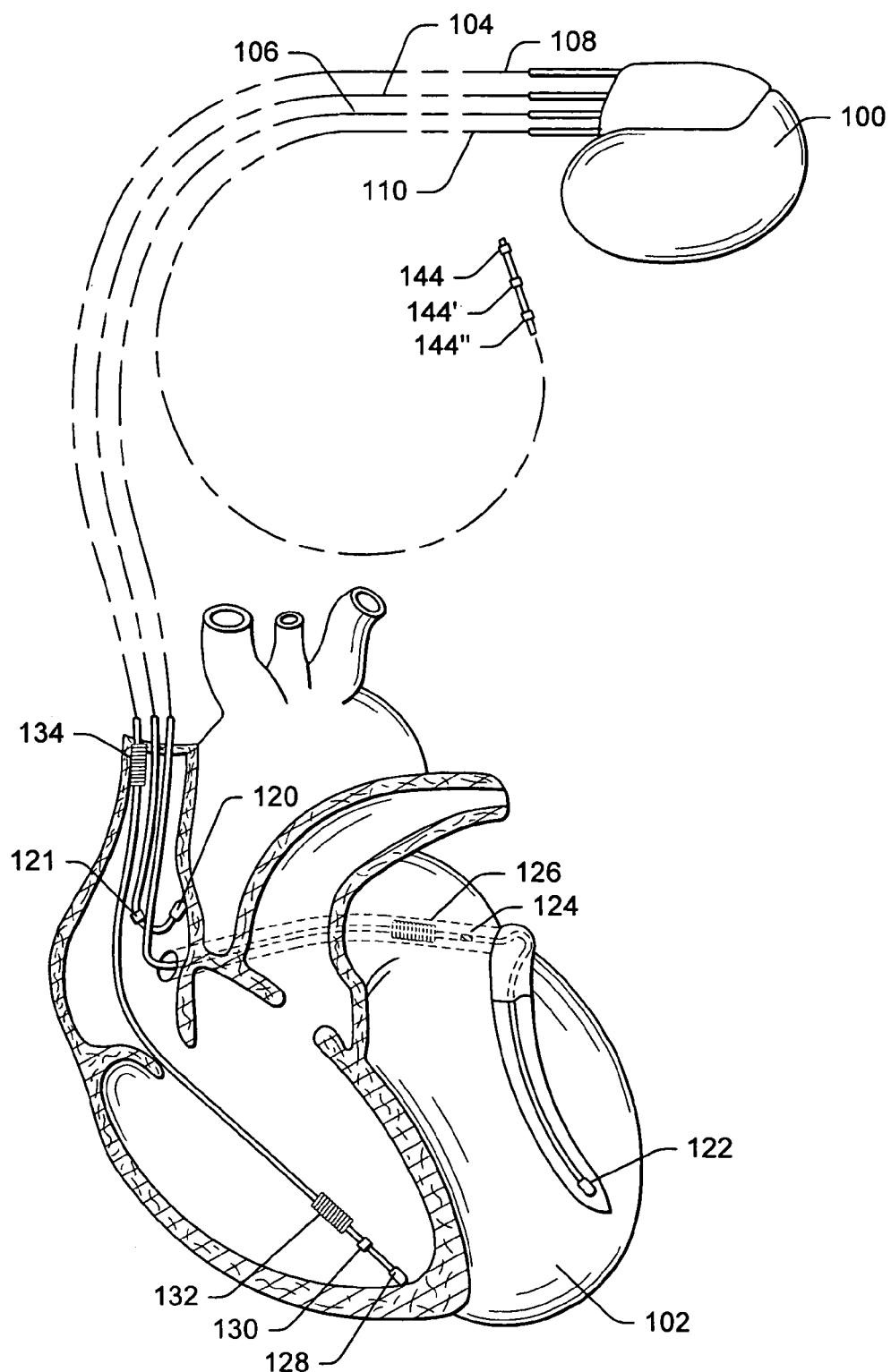
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of other stimulation and/or sensing. In addition, the device 100 includes a fourth lead 110 having, in this implementation, three electrodes 144, 144', 144" suitable for other stimulation and/or sensing. This lead may be positioned in and/or near a patient's heart or remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Figure 2:
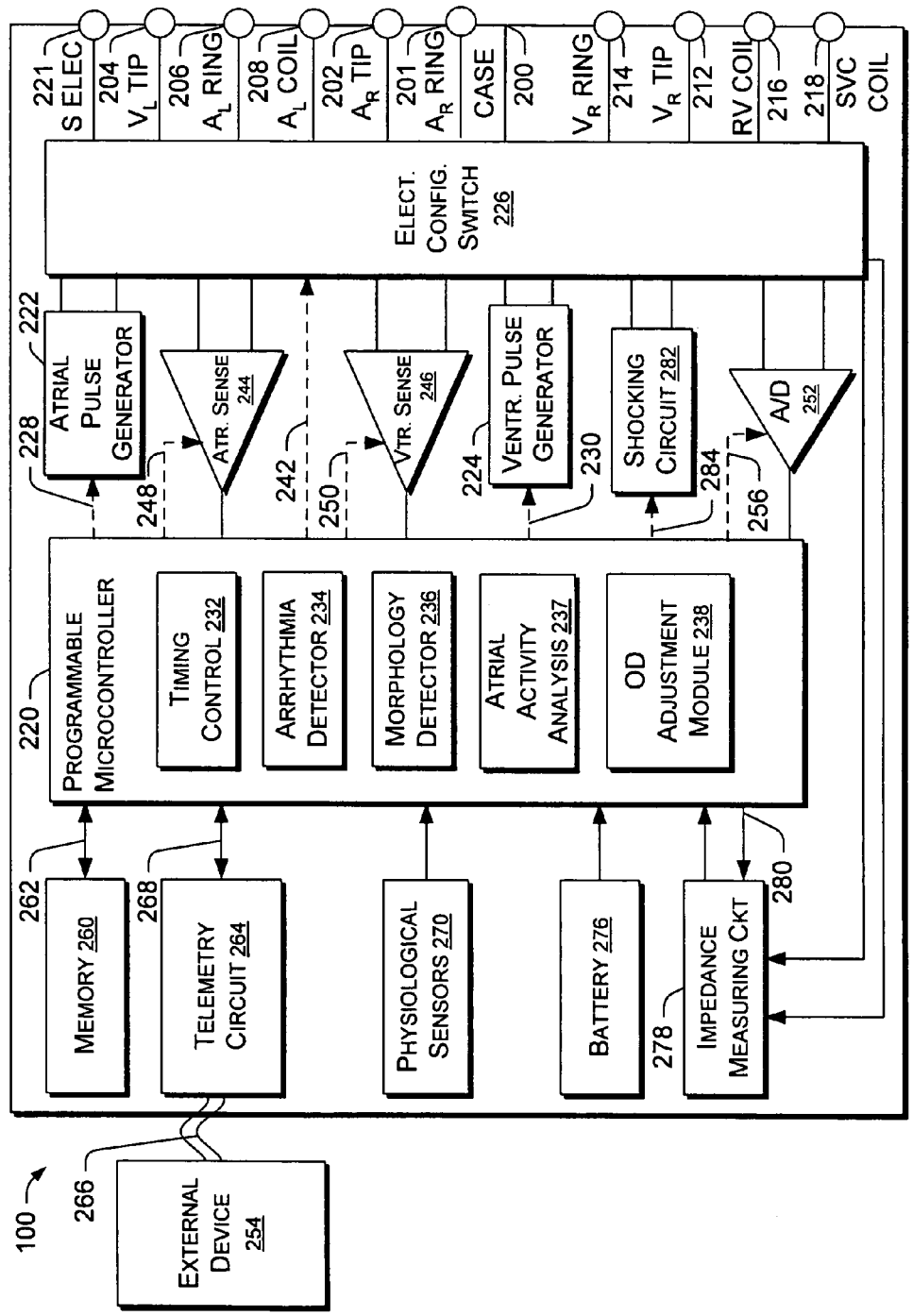
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable other stimulation and/or sensing electrodes is also possible via these and/or other terminals (e.g., via a terminal S ELEC 221).

To support right chamber sensing, pacing and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable other stimulation and/or sensing electrodes is also possible via these and/or other terminals (e.g., via the terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses. The microcontroller 220 may be a microprocessor capable of implementing or executing control logic.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module; the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an atrial activity analysis module 237. The atrial activity analysis module 237 optionally implements one or more methods for sensing, information analysis, and/or stimulation control related to atrial activity. For example, the atrial activity analysis module 237 optionally implements one or more of the exemplary methods described below.

Microcontroller 220 further includes an overdrive (OD) adjustment module 238 for performing a variety of tasks related to adjusting an OD rate. The exemplary module 238 optionally operates in conjunction with the atrial activity analysis module 237 to adjust OD rates, to enable OD adjustment, to disable OD adjustment and/or to terminate OD algorithms. Such a module 238 may also notify a clinician, a patient, a clinical device (e.g., computer, etc.) of OD status. The module 238 may include control logic operable in conjunction with the microcontroller 220.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR.SENSE) and ventricular (VTR.SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the other lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et. al), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3:
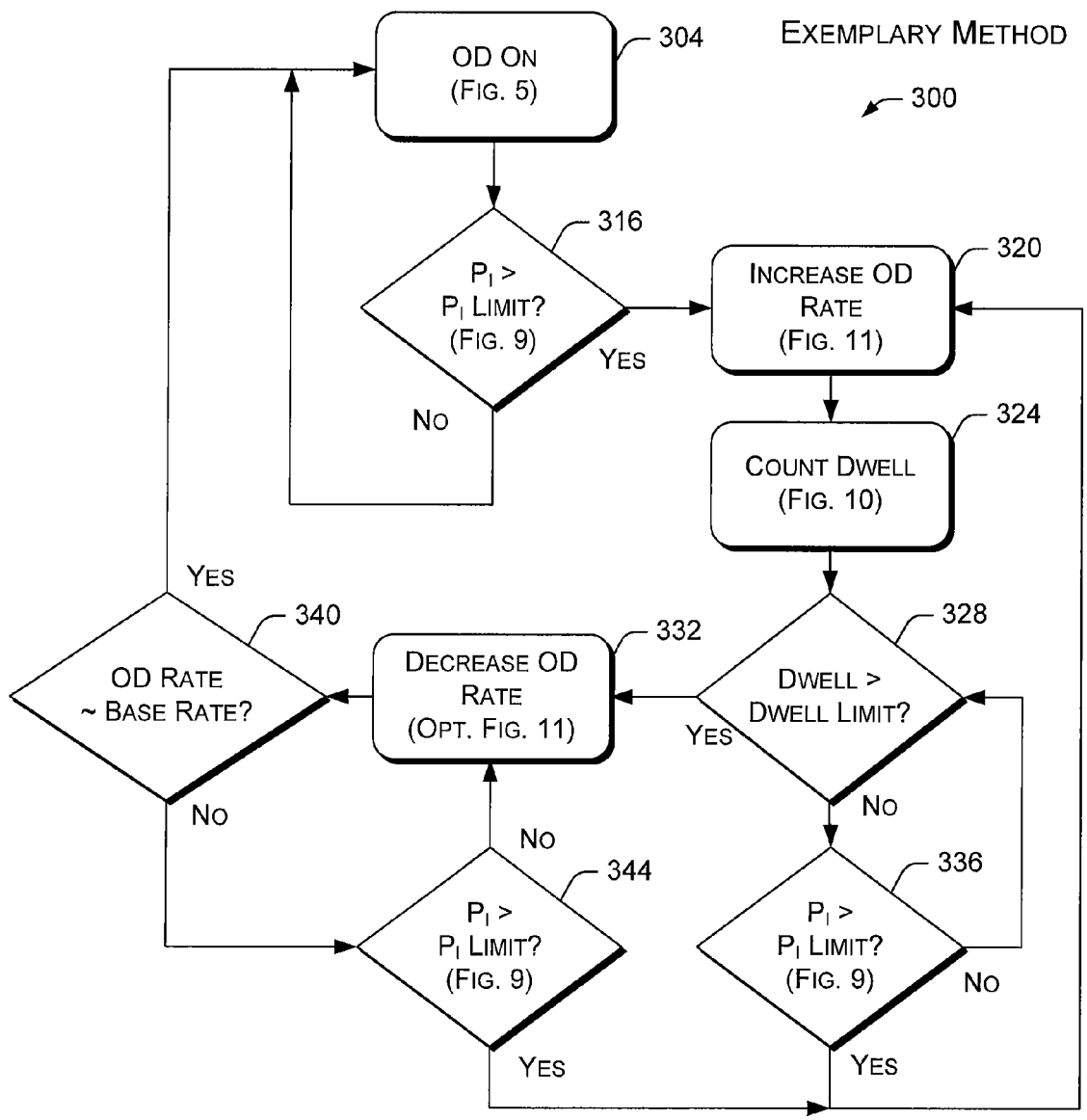
FIG. 3 is a block diagram of an exemplary method controlling overdrive (OD).

FIG. 3 shows an exemplary method 300 for controlling overdrive (OD). Such an exemplary method may be implemented using an implantable device that includes various features of the device 100 and/or other features. Various blocks within the exemplary method 300 refer to various exemplary methods described with reference to subsequent figures, which are described in more detail below.

The exemplary method 300 commences in an "on" block 304 wherein overdrive (OD) is switched on. The block 304 references FIG. 5, which shows an exemplary method 500 for determining whether to switch overdrive on. Thus, while the block 304 appears as an "on" block, it also represents a determination or decision of whether to implement an overdrive algorithm. Once "on" the overdrive algorithm monitors P-wave and determines a P-wave incidence ($P_i$) on a periodic or other basis. Various decision blocks rely on information such as P-wave incidence to call for appropriate control action (e.g., increasing OD rate, decreasing OD rate, etc.).

According to the exemplary method 300, a decision block 316 uses P-wave incidence to decide whether the P-wave incidence indicates a need for adjustment to overdrive delivery. For example, the decision block 316 may compare $P_i$ to a $P_i$ limit. The decision block 316 also references FIG. 9, which shows a P-wave incidence limit that is optionally a function of rate, for example, a rate that may vary from a base rate ($B_R$) or a rest rate ($R_R$) to a maximum rate ($MT_R$).

In the exemplary method 300, if the $P_i$ is less than the $P_i$ limit, then the method 300 continues at the OD on block 304 where monitoring of cardiac activity may continue (e.g., P-wave and/or other activity). If the P-wave incidence of the decision block 316 does not compare favorably to the incidence limit, then the exemplary method 300 may continue in an adjustment block 320 that acts to increase the overdrive rate (OD rate). As described herein, adjustments to overdrive rate may occur according to the exemplary method of FIG. 11. The exemplary method of FIG. 11 acts to prevent "rate runaway", which may occur in conventional overdrive methods. For example, in conventional overdrive methods, an increase in P-wave incidence may cause successive increases in overdrive rate in a manner that drives the overdrive rate to an upper rate limit.

Figure 10:
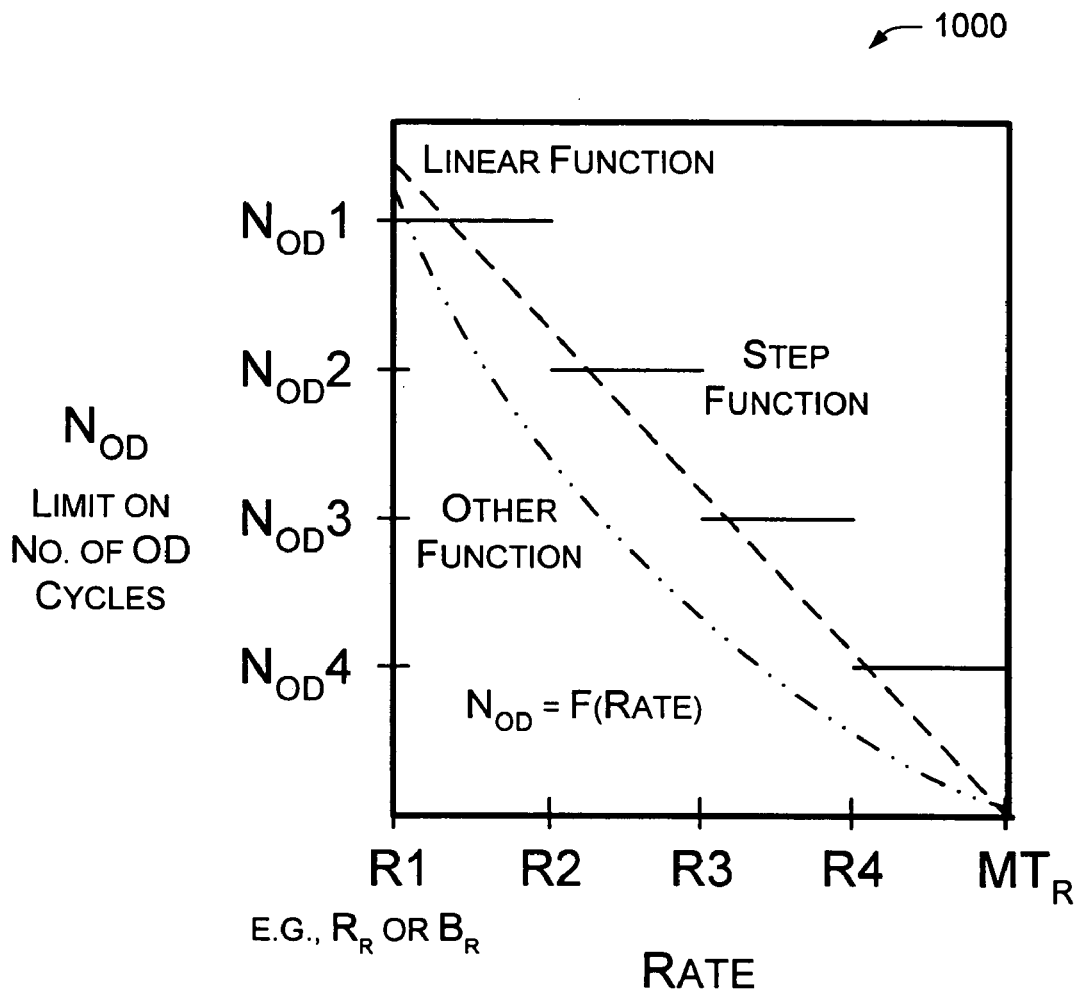
FIG. 10 is a plot of dwell limit ($N_{OD}$) versus overdrive (OD) rate according to several exemplary functions.

A dwell count block 324 follows the adjustment block 324, which references FIG. 10, which shows an exemplary method 1000 for adjusting a dwell limit or a maximum number of overdrive cycles ($N_{OD}$) as a function of rate, for example, a rate that may vary from a rest rate ($R_R$) or a base rate ($B_R$) to a maximum rate ($MT_R$). The number of overdrive cycles is termed dwell (e.g., $n_{OD}$) and refers typically to the number of consecutive overdrive cycles while $N_{OD}$ is a typically a limit on the number of consecutive overdrive cycles. Some conventional methods use a constant, non-varying dwell limit to decide whether a decrease in overdrive rate should occur. As described below, $N_{OD}$ may decrease as rate increases.

A decision block 328 follows that decides whether the dwell (e.g., $n_{OD}$) exceeds a dwell limit (e.g., $N_{OD}$). If the decision block 328 decides that the dwell does not exceed the dwell limit, then the exemplary method 300 enters another decision block 336, which references FIG. 9, as it pertains to comparing a P-wave incidence, $P_i$, to a P-wave incidence limit $P_i$ limit. If the decision block 336 decides that $P_i$ does not exceed the $P_i$ limit, then the exemplary method 300 continues at the dwell decision block 328; otherwise, the exemplary method 300 continues at the adjustment block 320, which may act to increase the overdrive (OD) rate.

Referring again to the decision block 328, if the dwell exceeds a dwell limit, then the exemplary method 300 continues in an adjustment block 332, which acts to decrease the overdrive (OD) rate. The adjustment block 332 references FIG. 11, which includes an exemplary method that is optionally used to decrease the overdrive (OD) rate.

After the adjustment to the overdrive (OD) rate per the adjustment block 332, a decision block 340 decides if the overdrive (OD) rate has decreased to reach a base rate ($B_R$) or some other low rate. If the overdrive (OD) rate reaches such a rate, then the exemplary method 300 continues in the commencement block 304. The commence block 304, as already mentioned, determines whether overdrive should be implemented.

Figure 9:
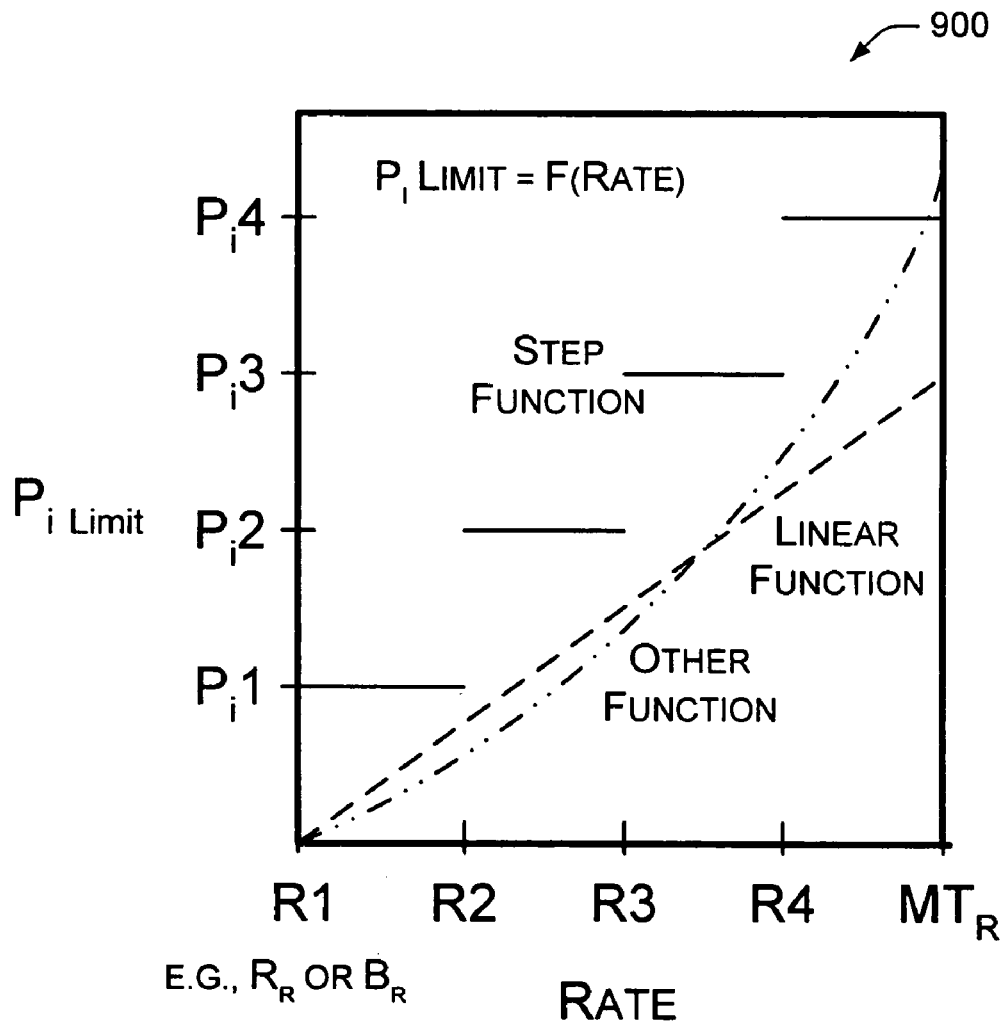
FIG. 9 is a plot of incidence limit ($P_i$) of atrial intrinsic events versus overdrive (OD) rate according to several exemplary functions.

Referring again to the decision block 340, if the overdrive (OD) rate has not decreased to some low rate, then the exemplary method 300 continues in a decision block 344, which references FIG. 9 as it pertains to P-wave incidence. The decision block 344 decides whether $P_i$ exceeds a $P_i$ limit and directs the exemplary method 300 to the adjustment block 332 as long as $P_i$ does not exceed the $P_i$ limit. However, if $P_i$ exceeds the $P_i$ limit, then the exemplary method 300 continues at the prior adjustment block 320, which may act to increase the overdrive (OD) rate.

While various P-wave incidence decision blocks are depicted in the block diagram, the P-wave incidence limit for the decision blocks 316, 336, 344 may differ. For example, upon a change in rate, the $P_i$ limit may vary as a function of rate. Further, a $P_i$ limit for one block may remain constant while a $P_i$ limit for another block varies according to one function and a $P_i$ limit for yet another block varies according to a different function or function parameters.

Figure 4:
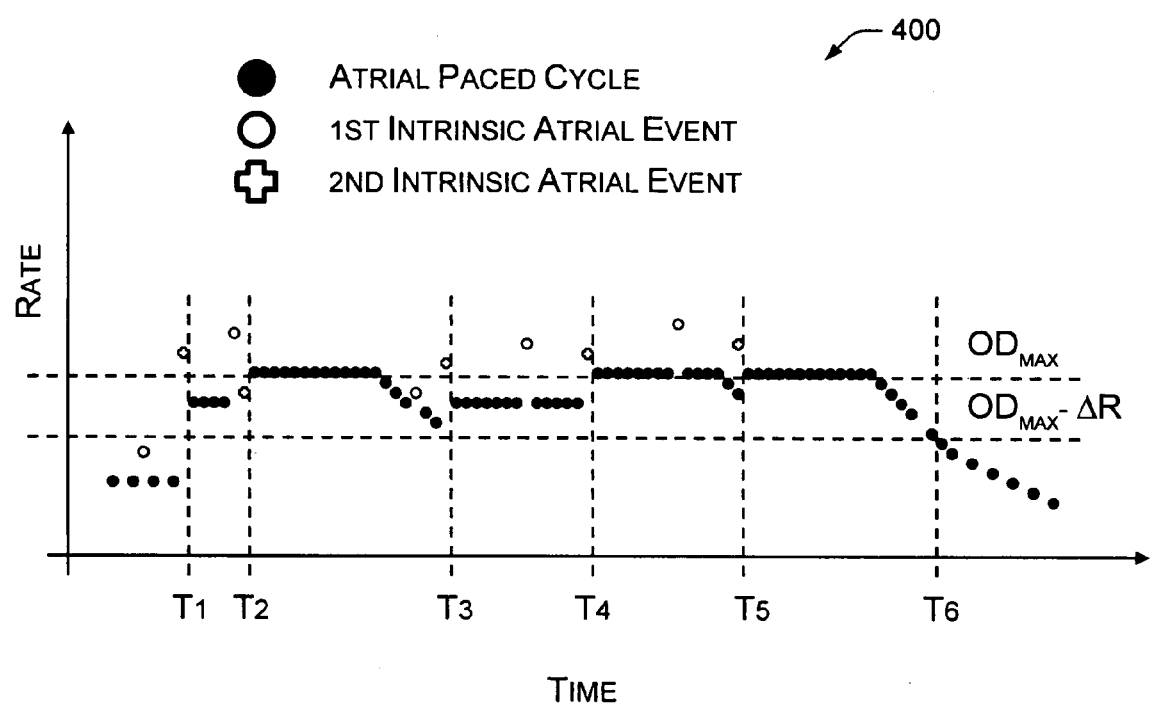
FIG. 4 is a plot of overdrive (OD) rate versus time wherein various rate changes responsive to detection of intrinsic atrial events (e.g., P-waves and/or PACs).

The exemplary method 300 of FIG. 3 referred to conventional problems associated with overdrive "runaway". FIG. 4 shows a plot 400 of OD rate versus time according to a conventional OD algorithm where rate runaway may occur. In this conventional example, the incidence limit is set at 2 events in 16 cycles (e.g., P wave incidence, intrinsic atrial event incidence, etc.). The conventional OD algorithm monitors intrinsic atrial activity over a predetermined number of cycles or less to determine whether to change OD rate. This particular OD algorithm increases the OD rate when two intrinsic atrial events occur within 16 cycles. For example, if the algorithm registers two intrinsic atrial events over 8 cycles, then the algorithm requests an increase in the OD rate and reinitiates the cycle count. However, if the algorithm does not request a further increase in OD rate within a certain number of cycles (e.g., a dwell limit of approximately 13 cycles), then the OD algorithm requests a ramp down of the OD rate.

Referring to FIG. 4, the plot 400 shows times T1, T2, T3, T4, T5, and T6. At T1, the algorithm requests an increase in the OD rate because the incidence limit was met. The change in OD rate is a step increase wherein the OD rate is increased from a value less than the OD rate minus a rate delta to a value greater than the OD rate minus the rate delta and less than the maximum OD rate. At T2, the algorithm requests another increase in the OD rate because two intrinsic atrial events occurred in 16 cycles (e.g., incidence limit met). In this instance, the step change in the OD rate increases the OD rate to the maximum OD rate. Typically, OD algorithms use a maximum OD rate as a limit to avoid implementation of excessive OD rates, which may be detrimental to the health of a patient and/or the longevity of the pacing device.

After adjustment to the maximum OD rate, the plot 400 indicates that the incidence limit was not met during the dwell of 13 cycles (e.g., dwell limit); therefore, the OD algorithm requested a ramp down in the OD rate. Note that monitoring of atrial activity does not cease during the ramp down, indeed, the plot 400 shows that two intrinsic atrial events were detected in 16 cycles (e.g., an incidence of 2 events in 16 cycles). Consequently, at T3, the OD algorithm requested a step increase in the OD rate. Further, at T4, the algorithm requested another increased in the OD rate, this time to the maximum OD rate. And, because two intrinsic atrial events were registered in 16 cycles, the algorithm maintained the maximum OD rate at T5. Eventually, after time T5, intrinsic atrial events ceased, noting that cessation of certain intrinsic atrial events can be an objective of OD pacing. Further, the rate continued to decrease according to the dwell as the incidence limit was not met.

In an extreme case, repeated salvos of intrinsic atrial events (e.g., PACs in particular) can drive the OD rate to the maximum allowed OD rate (e.g., a maximum sensor rate, etc.) as shown in FIG. 4 and maintain it at or near that rate for an extended time. This can cause uncomfortable symptoms for the patient and more importantly, pacing at high rates for sustained periods can cause tachycardia-induced heart failure.

While it may be appropriate to increase the OD rate in response to PACs, because overdrive pacing may act to suppress PACs (see, e.g., T2, T4); it is not necessarily appropriate to do so by the same mechanism by which the OD algorithm overdrives the sinus rate because additional considerations may exist. For example, the plot 400 indicates that OD may not effectively suppress intrinsic atrial events (e.g., PACs), i.e., up to T5, PACs continue to persist even though the OD rate is at or near the maximum OD rate. In addition, some patients might react to OD pacing with an increase in sinus rate, perhaps due to a catecholaminergic response, which, in turn, may produce positive feedback that maintains and/or increases the OD rate to its maximum. Under such circumstances, alternative action may be beneficial. For example, the exemplary method 300 of FIG. 3 shows various blocks that may provide more beneficial action and thereby reduce risk of OD rate runaway.

Figure 5:
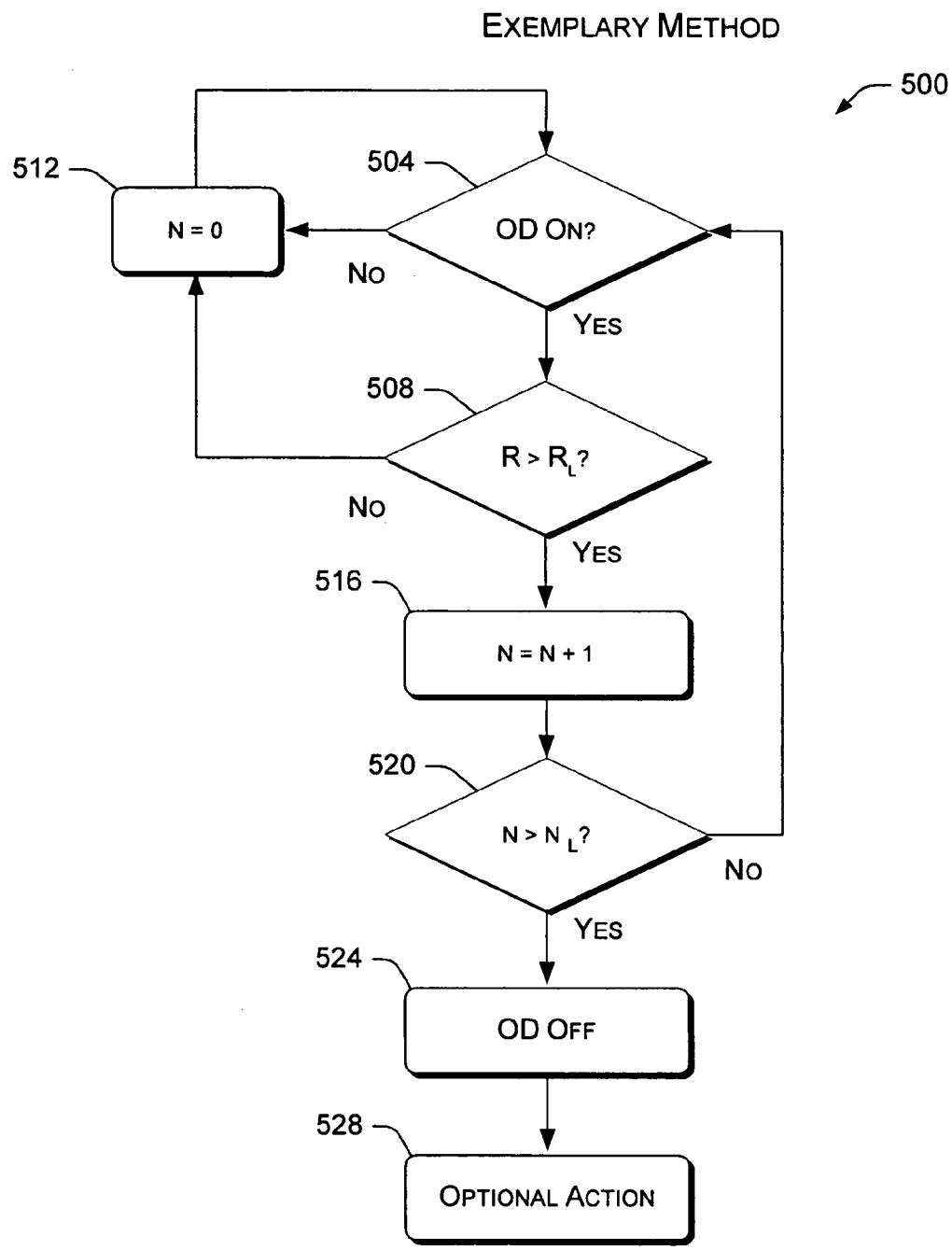
FIG. 5 is a block diagram of an exemplary method for turning off overdrive (OD) delivery.

While the exemplary method 300 of FIG. 3 refers generally to adjustments while overdrive is implemented, other exemplary methods described herein may disable overdrive pacing for a period of time or permanently (e.g., until a follow-up consultation). FIG. 5 shows an exemplary method 500 for disabling OD pacing upon occurrence of one or more criteria. These criteria may indicate whether OD pacing is excessive; thus, the exemplary method 500 may determine whether OD pacing is excessive and respond appropriately (e.g., by disabling OD pacing, etc.). The method 500 commences in a check block 504, which determines whether OD pacing is enabled. If the check block 504 determines that OD pacing is disabled, then the method continues in a set block 512, which sets a counter "n" to zero or some other appropriate value. The counter n may represent a count of events, time intervals, duration, etc. While in this example, n corresponds to a count, an incidence may be used. For example, a high incidence of a rate above $OD_{Max}-\Delta R$ (e.g., a number of occurrences over a give time or number of cycles) may cause appropriate action.

If the check block 504 determines that OD pacing is enabled, then the method 500 continues in a determination block 508. The determination block 508 determines whether the present OD rate, "R", is greater than an OD rate limit, "$R_L$". In general, $R_L$ is a high rate limit, for example, at or near a maximum tolerable OD rate. If the determination block 508 determines that R is less than or equal to $R_L$ then the method 500 continues in the set block 512. However, if the determination block 508 determines that R is greater than $R_L$, then the method 500 continues in an increment block 516. The increment block 516 increments the counter n, for example, n=n+1.

Next, another determination block 520 determines if the counter has exceeded a counter limit, for example, to determine if n is greater than a counter limit $n_L$. If the determination block 520 determines that n is less than or equal to $n_L$, the method 500 continues in the check block 504. However, if the determination block 520 determines that n is greater than $n_L$, then the method 500 continues in an OD off block 524, which disables OD pacing. Thereafter, the method 500 may continue at an optional action block 528 to take any of a variety of optional actions.

Figure 6:
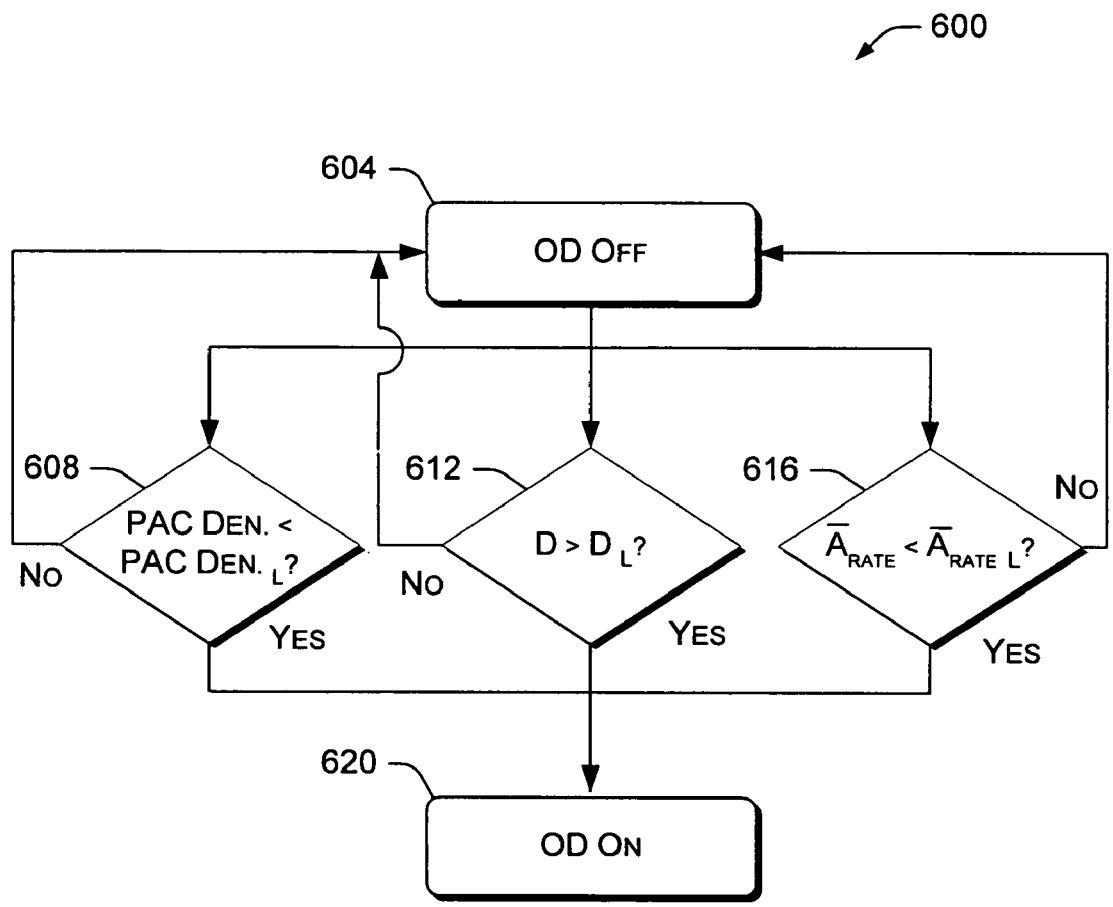
FIG. 6 is a block diagram of an exemplary method for turning on overdrive (OD) delivery.

Once disabled or turned "off", one or more exemplary mechanisms may be used to enable overdrive pacing or to turn overdrive pacing "on". FIG. 6 shows an exemplary method 600 that includes three optional actions, which may occur in series and/or in parallel with appropriate Boolean or other logic to thereby enable overdrive pacing. In general, each of the optional actions relies on occurrence of one or more conditions. Such conditions include, but are not limited to, a sensed physiologic condition, expiration of a time delay, a decrease in average atrial rate, a decrease in intrinsic atrial events (e.g., PACs, etc.), a decrease in density of intrinsic atrial events, and a decrease in density of certain events (e.g., PAC density, etc.).

As shown, the method 600 commences at the OD off block 604. Next, the method 600 enters a PAC density determination block 608, a delay block 612, and/or an atrial rate block 616. For example, the PAC density determination block 608 determines if the PAC density is greater than a PAC density limit. If the PAC density is greater than or equal to a PAC density limit, the method 600 continues at the OD off block 604. In general, this particular optional action keeps OD pacing off when a patient is experiencing high PAC density. This may alleviate additional concerns and/or call for additional action, other than OD pacing, aimed at terminating PACs. If the PAC density determination block 608 determines that the PAC density is less than the PAC density limit, then the method 600 continues at an OD on block 620, wherein OD pacing is enabled.

The delay determination block 612 determines if a delay timer, D, has reached a delay limit, $D_L$, for example, if D is greater than $D_L$, the delay timer has expired and the method 600 continues at the OD off block 604. If the delay timer has not expired, then the method 600 continues at the OD on block 620. While the delay timer in the block 612 pertains to time on, another delay timer may pertain to a time off. In the latter instance, such a delay may allow a patient to recover from a salvo of PACs and/or other events. For example, a delay timer may allow for an adjustment (natural and/or induced) to sympathetic and/or parasympathetic tone. In general, if a salvo of PACs is associated with increased sympathetic activity, a delay prevents OD pacing from enhancing sympathetic activity and may allow for a natural and/or an induced decrease in sympathetic activity.

The atrial rate determination block 616 determines if the intrinsic atrial rate (e.g., average intrinsic atrial rate, $A_{Rate}$) is less than an intrinsic atrial rate limit (e.g., an average intrinsic atrial rate limit $A_{Rate\ L}$). If the determination block 616 determines that $A_{Rate}$ is less than $A_{Rate\ L}$, then the method continues at the OD on block 620; however, if $A_{Rate}$ is greater than or equal to $A_{Rate\ L}$, then the method 600 continues at the OD off block 604. In general, if the intrinsic atrial rate is too high, then OD pacing may not be effective and may even be detrimental.

Figure 7:
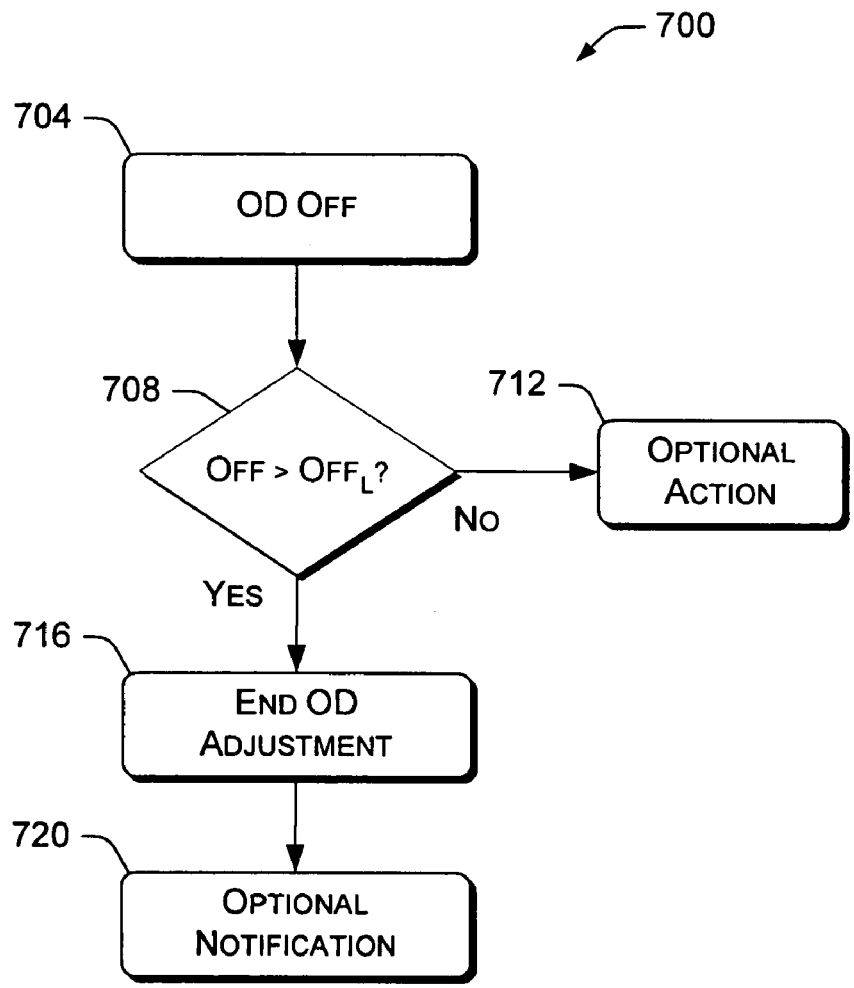
FIG. 7 is a block diagram of an exemplary method for disabling overdrive (OD) adjustment.

FIG. 7 shows another exemplary method 700 for disabling OD adjustment. The method 700 commences in an OD off block 704 and proceeds to an OD off limit check block 708. The OD off limit check block 708 checks an "off" counter that tracks how long and/or how frequent OD pacing has been disabled. If OD pacing has been disable for a long period of time and/or OD pacing has been disable frequently (e.g., per a off limit, $Off_L$), then in an end OD adjustment block 716, the method 700 ends any OD adjustment methods. Further, in a notification block 720, the method 700 may notify a patient, a clinician and/or a monitor that one or more OD adjustment methods have been disabled. Of course, any method may be optionally re-enabled at a later time. If the OD off limit check block 708 determines that no limit has been exceeded, then the method 700 may continue, for example, in an optional action block 712.

The counter in this example may represent a count of events, time intervals, duration, etc. While in this example, it corresponds to a count, an incidence may be used. For example, a high incidence of being turned off (e.g., a number of occurrences over a give time or number of cycles) may cause appropriate action.

Of course, a variety of other optional actions are possible. For example, any suitable parameter may be checked in a determination block to determine whether to enable and/or disable OD pacing and/or OD adjustment. In addition, any of the aforementioned optional actions may be linked through Boolean and/or other logic.

Also, limit cycles may occur wherein an on/off adjustment method cycles between on and off states. Should such a cycle persist for a predetermined number of cycles, then an exemplary method may take appropriate action, such as, but not limited to, disabling OD pacing and/or OD adjustment.

Figure 8:
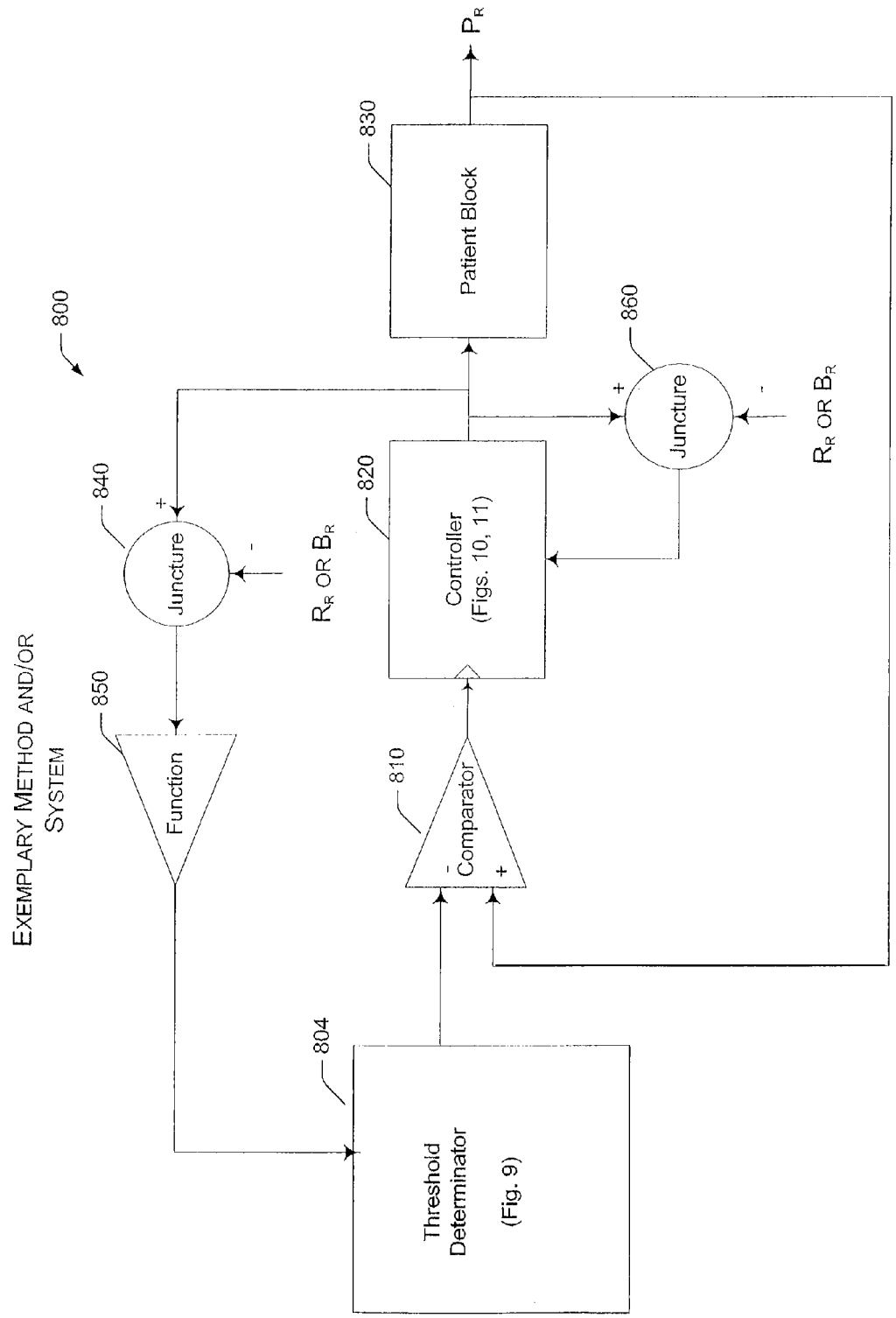
FIG. 8 is a block diagram of an exemplary method and/or system for adjusting overdrive (OD) rate.

FIG. 8 shows an exemplary method and/or system 800 for adjusting OD pacing. The exemplary method and/or system 800 include a threshold determination block 804, which determines a threshold incidence that is required to trigger action. In general, the threshold incidence rate represents a threshold incidence of intrinsic atrial events (e.g., P-waves and/or PACs) expressed as "X" events out of "Y" consecutive pacing cycles (e.g., a P-wave incidence). A particular conventional OD algorithm uses X equal to 2 intrinsic atrial events and Y equal to 16 cycles. However, in the exemplary method and/or system 800, X and/or Y may vary depending on any of a variety of factors. For example, as described in FIG. 9, below, P-wave incidence may vary as a function of OD pacing rate, typically in a range from a rest rate ($R_R$) or a base rate ($B_R$) to a maximum rate ($MT_R$). The incidence may vary based on a change in X, a change in Y and/or changes in X and Y. The threshold incidence may be determined based on characteristics of a patient 830, for example, according to a care provider. As shown in FIG. 8, the determination block 804 receives information regarding overdrive rate from block 820 via blocks 840 and 850. With respect to FIG. 9, the overdrive rate information may allow for selection of an appropriate threshold incidence (e.g., $P_{i\ Limit}$).

The threshold determination block 804 communicates with a comparison block 810. The comparison block 810 uses the threshold incidence and a measured incidence (or number of events, etc.) to determine if the threshold incidence has been exceeded. If the measured incidence or rate of intrinsic atrial events exceeds the threshold incidence or rate, an "overdrive sequence" is triggered.

The trigger signal is received by a control block 820, which controls the OD pacing rate. Control may include any of a variety of actions, such as, but not limited to, increasing the OD pacing rate by some amount, maintaining an increased OD rate for some number of OD cycles, and/or after a number of OD cycles has elapsed, reducing the OD rate according to some rate recovery function. Thus, the control block 820 may rely on relationships exhibited in the plot 1000 of FIG. 10 (e.g., dwell adjustment) and/or the plot 1100 of FIG. 11 (e.g., rate adjustment). The control block 820 may also make "on" and/or "off" control decisions, for example, relying on schemes such as 500 of FIG. 5, 600 of FIG. 6 and 700 of FIG. 7.

As appropriate, the control block 820 acts to output an OD pacing rate to the patient 830. Note that in this example the patient block 830 communicates intrinsic atrial event information (e.g., via a system component and/or other component and, e.g., an incidence of actual P-wave events, $P_R$) to the comparison block 810 and optionally an actual measured OD pacing rate to the comparison block 810. The intrinsic atrial event information may be a rate or other indicator useful in rate determination for purposes of a comparison to a threshold value.

The OD pacing rate from the control block 820 is also communicated to one or more junctures 840, 860. For example, junctures 840 and 860 allow for subtraction of a base rate ($B_R$) (or rest rate, $R_R$ where applicable) from the OD pacing rate to ease definition of exemplary functions shown in FIGS. 9, 10 and 11. For example, the OD pacing rate may aid in the determination of the number of pacing cycles to be used in the threshold incidence determination and/or the comparison.

The juncture 840 communicates the resulting rate value to a function block 850 which may use a function (e.g., a gain, etc.) to adjust the value prior to communicating the value to the threshold determination block 804. Of course, the function block 850 is optionally part of the threshold determination block 804. The juncture 860 communicates the resulting rate value to the control block 820, where it is optionally used to determine an amount of rate increase (e.g. per an atrial fibrillation suppression algorithm, etc.).

The control block 820 may operate as a module (e.g., the module 238 of FIG. 2) in conjunction with a microprocessor (e.g., the microprocessor 220 of FIG. 2). Inputs to the control block 820 may include the trigger signal, an upper rate limit, a lower rate limit, dwell (e.g., number of cycles), recovery interval, etc. The control block 820 may include one or more functions such as those described with respect to the plot 900 of FIG. 9, the plot 1000 of FIG. 10 and the plot 1100 of FIG. 11.

FIG. 9 shows a plot 900 of various exemplary functions of incidence limits of intrinsic atrial events ($P_{i\ Limit}$) versus OD rate (R), e.g., wherein $P_{i\ Limit}=f(R)$. Included in the functions are a step function, a linear function, and a nonlinear function or other function. The exemplary functions act to increase the incidence of intrinsic atrial events required to trigger an increase in OD rate (e.g., a positive adjustment in OD rate). Other functions may be used to trigger a decrease in OD rate (e.g., a negative adjustment in OD rate), such as the ramp down function described above.

As shown in FIG. 9, the step function steps from a $P_i 1$ incidence of intrinsic atrial events at R1 to a $P_i 2$ incidence intrinsic atrial events at R2, to a $P_i 3$ incidence of intrinsic atrial events at R3, to a $P_i 4$ incidence of intrinsic atrial events at R4 wherein R4>R3>R2>R1 and $P_i 4 > P_i 3 > P_i 2 > P_i 1$. If the number of cycles (e.g., Y) is held constant, then an increase in the threshold incidence or frequency of intrinsic atrial events required to trigger an increase in OD rate (e.g., positive adjustment in OD rate) represents an increase in the number of events (e.g., X) for the number of cycles (e.g., Y). The linear function and non-linear function also operate to increase the threshold incidence with increasing OD rate. Of course, other functions are possible. While this example refers to adjustment of the number of events (e.g., X), an adjustment may occur for the number of cycles (e.g., Y) or for both the number of events and the number of cycles (e.g., X and Y). In general, adjustments act to increase the threshold incidence with increasing OD rate. Thus, as OD rate increases, X may increase and/or Y may decrease to effectively increase the threshold incidence.

FIG. 10 shows a plot 1000 of various exemplary functions for dwell limit with respect to rate. For example, the plot 1000 shows exemplary relationships for a limiting number of OD cycles ($N_{OD}$) versus OD rate (R), e.g., wherein $N_{OD}=f(R)$. Included in the functions are a step function, a linear function, and a nonlinear function or "other" function. The exemplary functions act to decrease the number of OD cycles as used to decrease OD rate. Other functions may be used to trigger a decrease in OD rate (e.g., a negative adjustment in OD rate). In general, a decrease in OD rate occurs when a dwell count reaches a dwell limit for a given OD rate.

As shown in FIG. 10, the step function steps from $N_{OD}1$ cycles at R1 to $N_{OD}2$ cycles at R2, to $N_{OD}3$ cycles at R3, to $N_{OD}4$ cycles at R4 wherein R4>R3>R2>R1 and $N_{OD}4 < N_{OD}3 < N_{OD}2 < N_{OD}1$.

Figure 11:
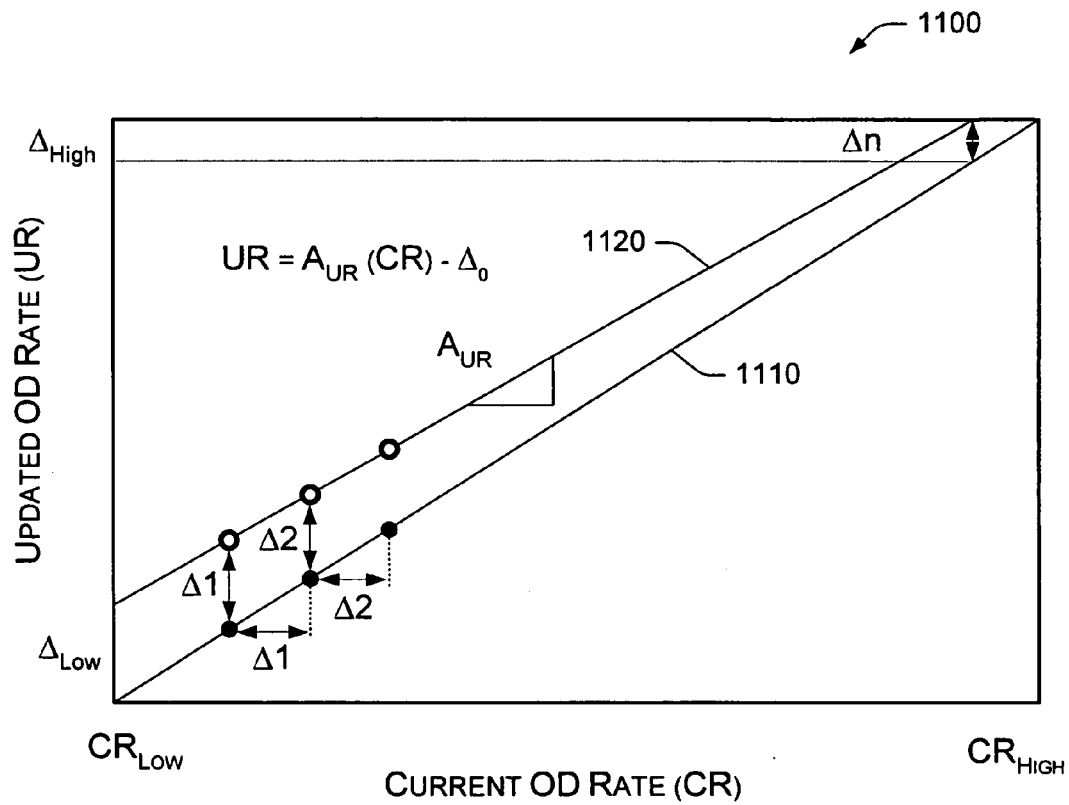
FIG. 11 is a plot of overdrive (OD) rate versus progression of rate increases for a slope adjustment method at two different slopes.

FIG. 11 shows a plot 1100 of an exemplary method for adjusting OD rate. The plot 1100 includes a lower line 1110 and an upper line 1120 plotted from a current low overdrive rate to a current high overdrive rate. In this example, the upper line 1120 has a slope $A_{UR}$, which may be used in determining an updated overdrive rate. At the current low rate ($CR_{Low}$), the two lines 1110, 1120 are separated by a rate difference $\Delta_{Low}$ while at the highest updated rate, the two lines 1110, 1120 are separated by a rate difference $\Delta_{High}$, wherein $\Delta_{Low}$ is generally greater than $\Delta_{High}$. The rate difference $\Delta_{High}$ may correspond to $\Delta n$, which represents a last update increment prior to reaching a maximum updated overdrive rate and/or maximum current overdrive rate.

For purposes of adjustments, an increase in overdrive rate is determined by locating the current overdrive rate on the lower line 1110 and then locating the updated overdrive rate on the upper line 1120, wherein the difference between the two rates is represented by $\Delta 1$, a rate adjustment step size. Accordingly, wherein $\Delta_{High}$ is less than $\Delta_{Low}$, the increases in overdrive diminish as the current overdrive rate increases. In this manner, the number of steps required to reach a maximum rate depends on the lines and the current overdrive rate. While lines are shown in the plot 1100, the upper line 1120 may be replaced by a curve, discrete steps, etc., that operate to reduce risk of runaway by decreasing rate increases as the current overdrive rate increases. For example, an exemplary implantable device may include control logic operable in conjunction with a microprocessor to adjust overdrive pacing rate using a rate adjustment step size wherein the rate adjustment step size decreases with respect to increasing overdrive pacing rate according to a predetermined schedule. Such a schedule may depend on patient characteristics wherein the control logic determines an appropriate schedule based on characteristics and/or a care provider selects a schedule appropriate for a given patient.

The exemplary method illustrated in the plot 1100 may also be used for adjustments that decrease overdrive rate wherein the current overdrive rate would be located on the line 1120 and the updated overdrive rate located on the line 1110 wherein the difference between the two rates represents the decrease in current rate for a given adjustment step. In this manner, the step size increases as the current rate approaches the low current rate. Again, as described above, the line 1120 may be replaced by a curve, discrete steps, etc. In general, for adjustments that increase rate or decrease rate, $\Delta_{Low}$ is greater than $\Delta_{High}$. Such parameters (e.g., $\Delta_{Low}$, $\Delta_{High}$, slopes, etc.), may be stored in memory and associated with patient condition and/or other information (e.g., model, look-up table, etc.). Thus, an exemplary implantable device may include control logic operable in conjunction with a microprocessor to adjust overdrive pacing rate using a rate adjustment step size wherein the rate adjustment step size increases with respect to decreasing overdrive pacing rate according to a predetermined schedule. Such a schedule may depend on patient characteristics wherein the control logic determines an appropriate schedule based on characteristics and/or a care provider selects a schedule appropriate for a given patient. Further such a schedule may serve to determine step size for increases and decreases in overdrive rate.

In general, the exemplary method illustrated in the plot 1100, generally acts to adjust overdrive pacing rate by decreasing a rate adjustment step size for successive increases in overdrive pacing rate and increasing a rate adjustment step size for successive decreases in overdrive pacing rate. Such an exemplary method may be implemented using control logic that operates in conjunction with a microprocessor such as the microprocessor 220 of FIG. 2. Further, such an exemplary method may include calling for delivery of overdrive pacing at an adjusted rate.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
    delivering overdrive pacing in accordance with an overdrive pacing rate;
    providing an overdrive pacing rate limit;
    determining a value of an overdrive pacing rate dwell limit as a function of a value of the overdrive pacing rate;
    determining a number of consecutive cycles of overdrive pacing at or above the overdrive pacing rate limit;
    comparing the number of consecutive cycles of overdrive pacing at or above the overdrive pacing rate limit to the dwell limit; and disabling overdrive pacing if the number of consecutive cycles of overdrive pacing at or above the overdrive pacing rate limit is greater than or equal to the dwell limit.

2. The method of claim 1 wherein the overdrive pacing rate limit is less than a maximum overdrive pacing rate.

3. The method of claim 1 wherein overdrive pacing is disabled for a period of time.

4. The method of claim 1 wherein overdrive pacing is enabled upon occurrence of an event.

5. The method of claim 1 wherein overdrive pacing is enabled upon occurrence of one or more conditions.

6. The method of claim 5 wherein the one or more conditions comprises a condition selected from a group consisting of a sensed physiologic condition, expiration of a time delay, a decrease in average atrial rate, a decrease in intrinsic atrial events and a decrease in density of events.

7. The method of claim 1 further comprising tracking one or more events selected from a group consisting of number of times overdrive pacing is disabled, duration that overdrive pacing is disabled, and frequency that overdrive pacing is disabled.

8. An implantable apparatus comprising:
   an input operative to receive information related to intrinsic cardiac activity;
   an output operative to deliver cardiac pacing stimuli at an overdrive pacing rate; and
   control logic configured to determine an overdrive pacing rate and a value of a dwell limit as a function of a value of the overdrive pacing rate, to determine a number of consecutive cycles of overdrive pacing at or above an overdrive pacing rate limit, to compare the number of consecutive cycles of overdrive pacing at or above the overdrive pacing rate limit to the dwell limit, and, to disable overdrive pacing if the number of consecutive cycles of overdrive pacing at or above the overdrive pacing rate limit is greater than or equal to the dwell limit.

9. The implantable apparatus of claim 8 and further comprising control logic to enable overdrive pacing.

10. The implantable apparatus of claim 8 wherein the control logic is operative to set the overdrive pacing rate limit to a value less than a maximum overdrive pacing rate.

11. The implantable apparatus of claim 8 wherein the control logic is operative to compare the incidence to an incidence limit.

12. The implantable apparatus of claim 8 wherein the control logic is operative to disable the overdrive pacing for a period of time.

13. The implantable apparatus of claim 8 wherein the control logic is operative to disable the overdrive pacing until occurrence of an event.

14. The implantable apparatus of claim 8 wherein the control logic is operative to disable the overdrive pacing until occurrence of one or more conditions.

15. A system comprising:
   means for providing overdrive pacing at an over drive pacing rate;
   means for providing an overdrive pacing rate limit;
   means for determining a value of an overdrive pacing rate dwell limit as a function of a value of the overdrive pacing rate;
   means for determining a number of consecutive cycles of overdrive pacing at or above the overdrive pacing rate limit;
   means for comparing the number of consecutive cycles of overdrive pacing at or above the overdrive pacing rate limit to the dwell limit; and
   means for disabling overdrive pacing when number of consecutive cycles of overdrive pacing at or above the overdrive pacing rate limit is greater than or equal to the dwell limit.

16. The system of claim 15 further comprising means for disabling the overdrive pacing for a period of time based on the means for deciding.

17. The system of claim 15 further comprising means for disabling the overdrive pacing, based on the means for deciding, until occurrence of an event.

* * * * *